United States Patent [19]
Climent Olmedo et al.

[11] Patent Number: 6,114,587
[45] Date of Patent: Sep. 5, 2000

[54] PROCESS AND CATALYST FOR THE SELECTIVE PRODUCTION OF α-ALKYLCINNAMALDEHYDE

[75] Inventors: Mª José Climent Olmedo; Rut Guil López; Sara Iborra Chornet; Jaime Primo Millo; Avelino Corma Canos, all of Valencia, Spain

[73] Assignees: Consejo Superior de Investigaciones Cientificas, Madrid; Universidad Politeonica de Valencia, Valencia, both of Spain

[21] Appl. No.: 09/171,158

[22] PCT Filed: Jan. 23, 1998

[86] PCT No.: PCT/ES98/00017

§ 371 Date: Feb. 2, 1998

§ 102(e) Date: Feb. 2, 1998

[87] PCT Pub. No.: WO98/35928

PCT Pub. Date: Aug. 20, 1998

[30] Foreign Application Priority Data

Feb. 12, 1997 [ES] Spain ................ 9700286

[51] Int. Cl.$^7$ .................................................. C07C 45/45
[52] U.S. Cl. .............................................. 568/433
[58] Field of Search .............................. 568/433

[56] References Cited

U.S. PATENT DOCUMENTS 5,475,162 12/1995 Brandvold et al. ............. 568/899
5,637,774 6/1997 Beavers ...................... 568/390

FOREIGN PATENT DOCUMENTS

| 0 392 579 | 10/1990 | European Pat. Off. . |
| 0 771 780 | 5/1997 | European Pat. Off. . |
| 2065086 | 9/1992 | Spain . |
| WO 94/27946 | 12/1994 | WIPO . |

OTHER PUBLICATIONS

Durr, 1956, Ann de Chim 13:85–114.

Durr, 1953, Academie des Sciences 28:1012+1014.

Mastagli et al., 1957, Academie des Sciences7:207–9.

Sarkar et al., 1986, Indian J. Chem.

Abenhaim et al., 1994, Synthetic Communications, 24(9):1199–1205.

*Primary Examiner*—Johann Richter
*Assistant Examiner*—Sreeni Padmanabhan
*Attorney, Agent, or Firm*—Klauber & Jackson

[57] ABSTRACT

The selective obtainment of α-alkyl cinnamaldehydes, such as Jasmine aldehyde is carried out by a process that involves two consecutive reactions: acetalization of an n-alkyl aldehyde by direct reaction with an alcohol or by transacetalization followed by the reaction between said acetal and aromatic aldehyde such as benzaldehyde using molecular sieves with regular pore distribution in the range of micro and mesopores and between 6 and 100 Å as acid catalysts.

12 Claims, No Drawings

PROCESS AND CATALYST FOR THE SELECTIVE PRODUCTION OF α-ALKYLCINNAMALDEHYDE

This is the U.S. National Stage Application of PCT/E598/00017 filed Jan. 23, 1998.

INTRODUCTION

The present invention describes the preparation of α-alkyl cinnamaldehydes and preferably, the preparation of α-n-amylcinnamaldehyde (Jasmine aldehyde), through aldolic condensation catalyzed by zeolite type solid acids.

α-n-amylcinnamadehyde is a substance with a violent scent and it is commonly used in perfumery. The production of α-n-amylcinnamaldehyde can be carried out through aldolic condensation between heptanal and benzaldehyde using alkaline catalysts.

A difficulty with aldol condensation is that both reagents can undergo side reactions giving rise to by-products that reduce the yield of alkyl cinnamaldehyde and that furthermore they can provide an unpleasant scent, thus reducing the quality of the perfume. One of these undesired reactions is self-condensation of n-alkyl aldehyde, which can be inhibited to a great extent, by keeping the concentration of this reagent relative to that of the benzaldehyde in the reaction mixture very low. Therefore, this methodology requires long addition times of heptanal, leading to the use of batch reactions with long reaction times and renders impractical the use of plug-flow continuous reactors.

Further by-products that are formed in these conditions are those resulting from the limited stability of benzaldehyde which tends to disproportionate via the Cannizzaro reaction to yield Benzes alcohol and benzoic acid, which in turn reacts with the alkaline catalyst, and therefore, causing the neutralization of the catalyst.

BACKGROUND OF THE INVENTION

A. Weissenborn in East German patent 11,191 (1956) describes a produce for the preparation of Jasmine aldehyde wherein the catalysts are Ni, Co or Fe salts of carboxylic acids. The reaction is carried out at the temperature range of 180–190° C., in the presence of toluene in order to facilitate azeotropic distillation of the water and the heptanal is added slowly to the reaction mixture. Yields around 80% of Jasmine aldehyde are obtained.

R. Mahrwald and H. Schick in East German patent DD 287,712 (1991) describe a procedure wherein the aldolic condensation between heptanal and benzaldehyde is accomplished in the presence of Titanium compounds (tetraisopropiltitanium) and toluene as the azeotropic agent. Yields around 56% of Jasmine aldehyde are obtained.

L. S. Payne in European patent 392,579 (1990) describes a procedure for the selective preparation of α-cinnamaldehydes by aldolic condensation in two phases, using glycols (especially ethylene glycol) as solvents and sodium or potassium hydroxides as catalysts. Yields around 90% of α-cinnamaldehyde are obtained.

P. Mastagli et al. in Bull. Soc. Chim. France, 1955, p. 268, describe the preparation of Jasmine aldehyde using anionic exchange resins (IR-4B) as catalysts. The yields obtained varied between 2 and 12%.

The same author describes in Compt. Rend. 1957 vol. 244, p. 207, a process starting from n-alkyl aldehyde and benzaldehyde acetals using as a catalyst a mixture of an acid catalyst (cationic exchange resin) and a basic catalyst (anionic exchange resin) in order to produce the hydrolysis and aldolic condensation respectively. The yields obtained varied between 5 and 28%.

A. Sakar et al. in Ind. J. Chem., 1986, vol. 25,p. 656 accomplish aldolic condensation using potassium carbonate and a phase transfer catalyst such as benzyltriethylammonium chloride. On the other hand, D. Abenhaim et al in Synthetic Comm., 1994, vol. 24, p. 1199 carry out condensation using the same type of catalysts but under microwave effect. In both cases yields around 80% of Jasmine aldehyde are obtained.

BRIEF DESCRIPTION OF THE INVENTION

This invention describes the selective obtainment of α-alkyl cinnamaldehydes and specifically, Jasmine aldehyde, by direct reaction between the acetal of n-alkyl aldehyde (heptanal) and benzaldehyde where zeolites and zeotypes with medium and large pore diameters with 10 and preferably 12 member rings, as well as mesoporous molecular sieves are used as acid catalysts.

The process involves a first acetalization step which is carried out directly with an alcohol or through transacetalization using trialkyl orthoformate (TOF) in the presence of the above-mentioned catalysts. The second step involves the elimination of the remaining alcohol or TOF by distillation and addition of benzaldehyde.

These acid catalysts subsequently cause slow hydrolysis of the acetal and mixed aldolic condensation, maintaining at all times a low concentration of the n-alkylaldhyde with respect to the benzaldehyde, thus obtaining the α-alkyl cinnamaldehydes with high yields and selectivities.

DETAILED DESCRIPTION OF THE INVENTION

The present invention relates the use of acid zeolites and mesoporous molecular sieves, that in a certain way could be assimilated to zeotype materials, as selective catalysts in the aldolic condensation between acetalizated n-alkyl aldehydes and benzaldehyde and in order to obtain α-alkyl cinnamaldehydes with yields higher than 80%.

The first stage of the process involves the acetalization of the aldehyde which takes place according to conventional procedures in a continuous or discontinuous batch reactor or in a continuous fixed or fluidized bed reactor filled with the catalyst. The reaction temperature ranges from 25 to 280° C. When the transacetalization method is used, the aldehyde and the corresponding trialkyl orthoformate molar ratio are between 1:1 and 1:10 preferably between 1:2 and 1:5.

Short chain saturated primary alcohols and glycols are the preferred alcohols. Methanol, ethanol, propanol and ethylene glycol are non-restrictive examples.

The second step of the reaction, and after distillation of the remaining alcohol or TOF, involves the addition of benzaldehyde to the reaction mixture. The heptanal/benzaldehyde molar ratio are between 1:1 and 1:10 m preferably between 1:2 and 1:5.

The reaction can be accomplished under inert atmosphere, such as nitrogen, and at a temperature ranging from 25 to 200° C., preferably between 50 and 150° C.

The amount of catalyst used is between 2 and 30% based on the weight of the n-alkyl aldehyde.

When the reaction is carried out in a batch reactor, at the end of the reaction the zeolite is filtered, washed with dichloromethane and the solvent is evaporated.

The catalysts used in the present invention are zeolites and zeotypes specifically of medium and large pore, preferably with 12 membered rings and mesoporous molecular sieves since the geometric constraints, due to the poor size, make it possible to obtain products with high selectivities from mixed aldolic condensation.

The zeolite catalysts that meet the previous specifications are, among others, the following (the initials between brackets being accepted by the International Zeolite Associations (see W. M. Meier and D. H. Olson in Atlas of Zeolites Structure Types, 1992)

Mordenite (MOR), Ofretite (OFF), Omega (MAZ), Beta (BEA), Y (FAU), SSZ-24 (AFI), ZSM-12 (AFI) and SSZ-42

New zeolites which combine channels of 10 MR with 12 MR (MCM-22), SSZ-26, SSZ-36, CIT-1 and zeotypes with extra large pore sizes (20–100 Å) such as M41S (such as MCM-41, (Beck et al. *JACS*, 114, 10834, (1992)), and amorphous mesoporous silica-alumina (SAM), with pore size in a narrow pore range (Bellussi et al.) *Stud. Surf. Sci.* 84, 93 (1994)) are also applicable.

The catalysts, prior to be used, have to be prepared in their acid form.

Preparation of the Acid Form

The preparation of the acid form is accomplished directly by exchange with an acid mineral when this is allowed by the zeolite stability, or if this is not possible, by an indirect method which consists in an exchange of its alkaline and alkaline earth cations by $NH_4^+$ through a treatment with aqueous solution of ammonium chloride followed by calcination, following conventional methods. It can also be prepared by exchange with di- or trivalent ions, followed by thermal treatment at temperatures between 100 and 600° C. for time intervals between 30 minutes and 6 hours.

On the other hand, the number of acid sites, the distribution of acid strength and the hydrophilic-hydrophobic characteristics of the catalyst can be controlled by varying its Si/Al ratio of the crystalline framework. The Al content of a zeolite can be modified directly during synthesis and this is not possible post-synthesis dealuminations are carried out. They mainly consist of the extraction of aluminum from the framework by acid treatment or using a complexing agent such as EDTA. Furthermore, if desired, it is possible to introduce silicon at the same time by chemical treatment with reagents such as $(NH_4)2F_6Si$ or $SiCl_4$.

EXAMPLES

Example 1

Acetalization of heptanal and subsequent condensation with benzaldehyde in the presence of zeolitic catalysts with a different structure.

Immediately before its use, the catalyst, in an amount equivalent to 10% (1.1 g) of the weight of the heptanal, is activated by heating at 100° C., under pressure of (1 mm Hg) for 2 h. After this time, the system is allowed to cool at room temperature and 11.5 g (0.1 mol) of heptanal dissolved in 150 ml. of methanol are added. The solution is heated at the reflux temperature of methanol during the time necessary to achieve an acetal (1,1-dimethoxyheptane) yield of around 90%. Thereafter, the methanol is evaporated and 10.6 g (0.1 mol) of benzaldehyde) are added. The condensation reaction is carried out under magnetic agitation at 125° C., under a nitrogen atmosphere for a reaction time between 4 and 16 h. After this time the catalyst is filtered and washed repeatedly with dichloromethane. The crude of the reaction is analyzed by gas chromatography-mass spectrometry. The Jasmine aldehyde yield in molar %, for the different catalysts, is:

| Catalyst | Jasmine Aldehyde Yield (%) |
|---|---|
| MCM-41 | 87 |
| SAM | 83 |
| HY | 75 |

Example 2

Acetalization and condensation between benzaldehyde and 1,1-dimethoxyheptane in the presence of MCM-41 catalyst with different benzaldehyde/heptanal molar ratios.

In the same conditions as in Example 1, the reaction is carried out in the presence of MCM-41 catalyst with a Si/Al ratio of 14, and using different benzaldehyde/heptanal molar ratios (1:1, 1:3 and 1:5). The results show that the variation of the ratio of reagents has little influence on the selectivity to jasmine aldehyde, obtaining final yields in the neighborhood of 85%.

Example 3

Influence of the temperature on the condensation reaction in the presence of MCM-41.

In the same conditions as in Examples 1 and 2, the reaction is carried out in the presence of MCM-41 catalyst with a Si/Al ratio of 14 at different reaction temperatures. The Jasmine aldehyde yield obtained after one hour reaction time is shown on the table:

| Temperature (° C.) | Jasmine Aldehyde Yield (%) |
|---|---|
| 100 | 10 |
| 125 | 60 |
| 140 | 70 |

What is claimed is:

1. A process for the preparation of α-alkyl cinnamaldehydes, the process comprising a first step of acetalization of an n-alkyl aldehyde by direct reaction of the aldehyde with an alcohol or transacetalization with trialkyl orthoformate for obtaining n-alkyladehyde acetal, and a second step wherein the acetal and benzaldehyde or a substituted benzaldehyde, are subjected to condensation using an acid catalyst in the absence of a basic catalyst, wherein the acid catalyst is an acid form of a molecular sieve having a pore distribution of 6 to 100 Å selected from the group consisting of mesoporous molecular sieves, microporous molecular sieves and molecular sieves having micropores and mesopores.

2. A process according to claim 1 wherein the molecula sieve is a zeolite selected from the group consisting of Beta, Y, Mordenite, Omega, MFI, SSZ-24, SSZ-26, SSZ-33, CIT-1, SSZ-42, MCM-22 zeolites and isomorphic substitutions thereof with trivalent ions selected from Al, B, Ga, Fe.

3. A process according to claim 2 wherein the zeolite has a framework Si/T''' ratio in a range of 6 and 400 wherein T''' refers to trivalent elements.

4. A process according to claim 1 wherein the molecular sieve is a microporous silica-aluminum phosphate selected from the group consisting of SAPO-5, ALPO-8 and VPI-5 and SAPO-37.

5. A process according to claim 1 wherein the molecular sieve is a mesoporous material.

6. A process according to claim 1 wherein the condensation is carried out at a temperature between 25 and 200° C. and a reaction time of between 10 minutes and 24 hours.

7. A process according to claim 1 wherein the alcohol used in the acetalization is selected from the group consisting of methanol, ethanol, propanol, ethylene glycol and propylene glycol.

8. A process according to claim 1, wherein the n-alkyl aldehyde acetal is a RCHO acetal, wherein R is a linear or branched, saturated or unsaturated chain having between 2 and 20 carbon atoms.

9. A process according to claim 5, wherein the mesoporous material is selected from the group consisting of M41S and SAM.

10. A process according to claim 6, wherein the reaction time is between 10 minutes and 5 hours, and the molar ratio between benzaldehyde and n-alkylaldehyde is from 1:1 to 1:10.

11. A process according to claim 6, wherein the reaction time is between 10 minutes and 5 hours, and the molar ratio between benzaldehyde and n-alkylaldehyde is between 1:1 and 1:5.

12. A process according to claim 3, wherein the framework $Si/T'''$ ratio is between 10 and 200.

* * * * *

UNITED STATES PATENT AND TRADEMARK OFFICE
CERTIFICATE OF CORRECTION

PATENT NO. : 6,114,587
DATED : September 5, 2000
INVENTOR(S) : M$^a$ Jose Climent Olmedo et al It is certified that error appears in the above-identified patent and that said Letters Patent is hereby corrected as shown below:

On the face of the Patent, please change the Section 371 Date and the Section 102(e) Date from "February 2, 1998" to read --February 2, 1999--

Signed and Sealed this

Seventeenth Day of April, 2001

Attest:

NICHOLAS P. GODICI

*Attesting Officer*   *Acting Director of the United States Patent and Trademark Office*